United States Patent
Nadeau et al.

[11] Patent Number: 5,958,700
[45] Date of Patent: *Sep. 28, 1999

[54] DETECTION OF NUCLEIC ACIDS BY FLUORESCENCE QUENCHING

[75] Inventors: James G. Nadeau, Chapel Hill; J. Bruce Pitner; C. Preston Linn, both of Durham; James L. Schram, Knightdale, all of N.C.

[73] Assignee: Becton, Dickinson and Company, Franklin Lakes, N.J.

[*] Notice: This patent is subject to a terminal disclaimer.

[21] Appl. No.: 09/237,510

[22] Filed: Jan. 26, 1999

Related U.S. Application Data

[63] Continuation of application No. 08/865,675, May 30, 1997.

[51] Int. Cl.[6] .............................. C12Q 1/68; C12P 19/34; C07H 21/04
[52] U.S. Cl. ........................... 435/6; 435/91.2; 536/24.3; 536/25.3; 536/25.32
[58] Field of Search ..................... 435/6, 91.2; 536/24.3, 536/25.3, 25.32

[56] References Cited

U.S. PATENT DOCUMENTS

| | | | |
|---|---|---|---|
| 5,547,861 | 8/1996 | Nadeau et al. | 435/91.2 |
| 5,550,025 | 8/1996 | Walker | 435/6 |
| 5,593,867 | 1/1997 | Walker et al. | 455/91.2 |
| 5,607,834 | 3/1997 | Bagwell | 435/6 |

FOREIGN PATENT DOCUMENTS

| | | |
|---|---|---|
| 5-15439 | 3/1993 | Japan . |
| WO 96/21144 | 7/1996 | WIPO . |

OTHER PUBLICATIONS

L. E. Morrison "Detection of Energy Transfer and Fluorescence Quenching" *Nonisotopic DNA Probe Techniques* Academic Press, pp. 311–352 (1992).

S. S. Ghosh, et al. "Real time kinetics of restriction endonuclease cleavage monitored by fluorescence resonance energy transfer" *Nucl. Acids Res.* 22:3155–3159 (1994).

L. G. Lee, et al. "Allelic discrimination by nick-translation PCR with fluorogenic probes" *Nucl. Acids Res.* 21:3761–3766 (1993).

S. P. Lee, et al. "A Fluorometric Assay for DNA Cleavage Reactions Characterized with BamHl Restriction Endonuclease" *Anal. Biochem.* 220:377–383 (1994).

*Primary Examiner*—John L. LeGuyader
*Assistant Examiner*—Mark L. Shibuya
*Attorney, Agent, or Firm*—Donna R. Fugit

[57] ABSTRACT

A detector oligonucleotide having a sequence which forms an intramolecularly base-paired secondary structure is described for use in detecting nucleic acid target sequences and target sequence amplification. The detector oligonucleotide is further modified by linkage to two dyes which form a donor/acceptor dye pair. The two dyes are positioned on the detector oligonucleotide such that they are in close spatial proximity in the base-paired, folded secondary structure, thereby causing quenching of donor fluorescence. The detector oligonucleotide may optionally further comprise a restriction endonuclease recognition site (RERS) which remains partially or entirely single-stranded in the base-paired secondary structure. The RERS is flanked by the two dyes. In the presence of target, the base-paired secondary structure is unfolded or linearized, increasing the distance between the donor and acceptor dyes and causing a change in fluorescence of the donor and/or the acceptor. If an RERS is present, it is rendered double-stranded in the presence of target, allowing cleavage or nicking by a restriction endonuclease and separation of the two dyes onto separate nucleic acid fragments. This may further contribute to the magnitude of the change in fluorescence.

24 Claims, 2 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 48 base pairs
      (B) TYPE: nucleic acid
      (C) STRANDEDNESS: single
      (D) TOPOLOGY: linear    (xi) SEQUENCE DESCRIPTION: SEQ ID NO:1:

TAGCACCCGA GTGCTAGAGT CTTCAAATAT CAGAGCTTTA CCTAACAA          48

(2) INFORMATION FOR SEQ ID NO:2:

(i) SEQUENCE CHARACTERISTICS:
      (A) LENGTH: 45 base pairs
      (B) TYPE: nucleic acid
      (C) STRANDEDNESS: single
      (D) TOPOLOGY: linear    (xi) SEQUENCE DESCRIPTION: SEQ ID NO:2:

ACCGCATCGA ATCGATGTCT CGGGTAGAAA ATCGCATGCA AGATA            45

(2) INFORMATION FOR SEQ ID NO:3:

(i) SEQUENCE CHARACTERISTICS:
      (A) LENGTH: 46 base pairs
      (B) TYPE: nucleic acid
      (C) STRANDEDNESS: single
      (D) TOPOLOGY: linear    (xi) SEQUENCE DESCRIPTION: SEQ ID NO:3:

CGATTCCGCT CCAGACTTCT CGGGAGCTGC CTCAGAATAT ACTCAG           46

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single
      (D) TOPOLOGY: linear -continued (xi) SEQUENCE DESCRIPTION: SEQ ID NO:4:

TAAACATGAA AACTCGTTCC G                                        21

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

TTTTATGATG AGAACACTTA AACTCA                                   26

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:6:

TTGTTAGGTA AAGCTCTGAT ATTTGAAGAC TCATCTGAGT AACCAGAC           48

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:7:

TTGTTAGGTA AAGCTCTGAT ATTTGAAGAC TCTACTGAGT AACCAGAC           48

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:8:

TTGTTAGGTA AAGCTCTGAT ATTTGAAGAC TCTAGCGAGT AACCAGAC           48

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:9:

TTGTTAGGTA AAGCTCTGAT ATTTGAAGAC TCTAGCACGT AACCAGAC           48

DETECTION OF NUCLEIC ACIDS BY FLUORESCENCE QUENCHING

This is a continuation of U.S. application Ser. No. 08/865,675, filed May 30, 1997.

FIELD OF THE INVENTION

The invention relates to methods for detecting nucleic acid target sequences, and in particular to detection methods employing fluorescence quenching.

BACKGROUND OF THE INVENTION

Sequence-specific hybridization of oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) for detection of probe hybridization rather than direct detection of fluorescence intensity. Fluorescence energy transfer occurs between a donor fluorophore and an acceptor dye (which may or may not be a fluorophore) when the absorption spectrum of one (the acceptor) overlaps the emission spectrum of the other (the donor) and the two dyes are in close proximity. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Förster (1948. *Ann. Phys.* 2, 55–75). The distance between donor and acceptor dyes at which energy transfer efficiency is 50% is referred to as the Förster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Typically, FET and related methods have relied upon monitoring a change in the fluorescence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the acceptor. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352).

Alternatively, the donor and acceptor may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, a self-complementary oligonucleotide labeled at each end may form a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. Tyagi and Kramer (1996. *Nature Biotech.* 14, 303–308) describe a hairpin labeled as described above with a detector sequence in the loop between the self-complementary arms of the hairpin which form the stem. The base-paired stem must melt in order for the detector sequence to hybridize to the target and cause a reduction in quenching. A "double hairpin" probe and methods of using it are described by B. Bagwell, et al. (1994. *Nucl. Acids Res.* 22, 2424–2425; U.S. Pat. No. 5,607,834). These structures contain the target binding sequence within the hairpin and therefore involve competitive hybridization between the target and the self-complementary sequences of the hairpin. Bagwell solves the problem of unfavorable hybridization kinetics by destabilizing the hairpin with mismatches, thus favoring hybridization to the target. In contrast to these publications, the detector oligonucleotides of the invention have the target binding sequence wholly or partially in a single-stranded "tail" region rather than fully contained within the intramolecularly base-paired secondary structure. The secondary structure (e.g., a hairpin) therefore need not unfold in order to initially hybridize to the target. Hybridization of the single-stranded tail is not competitive so the kinetics of the reaction favor hybridization to the target. Hybridization of the detector oligonucleotide through the single-stranded tail also increases the local concentration of target, thereby driving any subsequent unfolding of the secondary structure. By shifting the kinetics of the reaction to better favor unfolding in the presence of target, the methods of the invention allow the use of perfectly base-paired secondary structures which would otherwise be too stable to be effective for target detection.

Homogeneous methods employing energy transfer or other mechanisms of fluorescence quenching for detection of nucleic acid amplification have also been described. R. Higuchi, et al. (1992. *Biotechnology* 10, 413–417) disclose methods for detecting DNA amplification in real-time by monitoring increased fluorescence for ethidium bromide as it binds to double-stranded DNA. The sensitivity of this method is limited because binding of the ethidium bromide is not target specific and background amplification products are also detected. L. G. Lee, et al. (1993. *Nuc. Acids Res.* 21, 3761–3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target. There is no specific disclosure of how a restriction endonuclease would be used in a fluorescence energy transfer system.

Energy transfer and other fluorescence quenching detection methods have also been applied to detecting a target sequence by hybridization of a specific probe. Japanese Patent No. 93015439 B discloses methods for measuring polynucleotides by hybridizing the single-stranded target to a single-stranded polynucleotide probe tagged with two labels which form an energy transfer pair. The double-stranded hybrid is cleaved by a restriction enzyme between the labels and fluorescence of one of the labels is measured. A shortcoming of this method is that the restriction site in the probe must also be present in the target sequence being detected. The patent does not describe adaptation of the probe for use in assays where the target sequence does not contain an appropriate restriction site or where cleavage of the target is not desired. S. S. Ghosh, et al. (1994. Nucl. Acids Res. 22, 3155–3159) describe restriction enzyme catalyzed cleavage reactions of fluorophore-labeled oligonucleotides which are analyzed using fluorescence resonance energy transfer. In these assays, the complementary oligonucleotides are hybridized to produce the double-stranded restriction site, and one of the fluorescent labels is linked to each of the two strands (i.e., they are not linked to the same strand, see FIG. 1 of Ghosh, et al.). S. P. Lee, et al. (1994. Anal. Biochem. 220, 377–383) describe fluorescence "dequenching" techniques using restriction endonucleases to cleave double-stranded DNA. However, these methods relate to assays employing only a single fluorescent label which is quenched by interaction with the DNA, not by fluorescence energy transfer from a second fluorescent label. Hybridization of the labeled oligonucleotide to its complement and cleavage of the double-stranded restriction site relieved non-transfer quenching of the label and quenched fluorescence was totally recovered.

Signal primers (also referred to as detector probes) which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins. Examples of detection methods for use with signal primers are described in U.S. Pat. No. 5,550,025 (incorporation of lipophilic dyes and restriction sites) and U.S. Pat. No. 5,593,867 (fluorescence polarization detection).

SUMMARY OF THE INVENTION

The present invention employs a detector oligonucleotide for detection of nucleic acid target sequences by fluorescence quenching mechanisms. The otherwise single-stranded detector oligonucleotide is selected such that it forms an intramolecularly base-paired secondary structure under the selected reaction conditions for primer extension or hybridization to the target. The detector oligonucleotide is further modified by linkage to two dyes which form a donor/acceptor dye pair. The two dyes are positioned on the detector oligonucleotide such that they are in close spatial proximity in the base-paired, folded secondary structure and the fluorescence of the donor dye is quenched. The detector oligonucleotide may further comprise a restriction endonuclease recognition site (RERS) between the two dyes which remains partially or entirely single-stranded in the base-paired secondary structure. As the detector oligonucleotide is initially single-stranded except for the base-paired portion of the secondary structure and remains single-stranded with the secondary structure folded in the absence of target, donor fluorescence is quenched. In the presence of target, however, the detector oligonucleotide is unfolded or linearized, increasing the distance between the donor and acceptor dyes and causing a change in fluorescence. If an RERS is present in the portion of the detector oligonucleotide between the two dyes, it is uncleavable or unnickable in the absence of target. The RERS becomes double-stranded in the presence of target, however, allowing cleavage or nicking by the restriction endonuclease and separation of the two dyes onto separate nucleic acid fragments. Cleavage or nicking further contributes to the change in fluorescence which indicates target amplification or the presence of the target sequence.

In alternative exemplary embodiments, the invention employs the detector oligonucleotide as a signal primer in target amplification reactions for detecting target sequence amplification, in non-amplification based primer extension methods for detection of target sequences and in hybridization reactions for detection of target sequences.

DETAILED DESCRIPTION OF THE INVENTION

The present invention employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, an RERS is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as a indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

Certain terms used herein are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described in U.S. Pat. No. 5,455,166; U.S. Pat. No. 5,270,184 and; EP 0 684 315. A hemimodified recognition site is a double stranded recognition site for a restriction endonuclease in which one strand contains at least one derivatized nucleotide which causes the restriction endonuclease to nick the primer strand rather than cleave both strands of the recognition site. Usually, the primer strand of the hemimodified recognition site does not contain derivatized nucleotides and is nicked by the restriction endonuclease. Alternatively, the primer may contain derivatized nucleotides which cause the unmodified target strand to be protected from cleavage while the modified primer strand is nicked. Such restriction endonucleases can be identified in routine screening systems in which a derivatized dNTP is incorporated into a restriction endonuclease recognition site for the enzyme. Preferred hemimodified recognition sites are hemiphosphorothioated recognition sites for the restriction endonucleases Hincll, BsoBI and BsrI. The amplification primer also comprises a 3'-OH group which is extendible by DNA polymerase when the target binding sequence of the amplification primer is hybridized to the target sequence. For the majority of the SDA reaction, the amplification primer is responsible for exponential amplification of the target sequence.

As no special sequences or structures are required to drive the amplification reaction, amplification primers for PCR may consist only of target binding sequences. Amplification primers for 3SR and NASBA, in contrast comprise an RNA polymerase promoter near the 5' end. The promoter is appended to the target sequence and serves to drive the amplification reaction by directing transcription of multiple RNA copies of the target.

Extension products are nucleic acids which comprise a primer or a portion of a primer and a newly synthesized strand which is the complement of the target sequence downstream of the primer binding site. Extension products result from hybridization of a primer to a target sequence and extension of the primer by polymerase using the target sequence as a template.

The terms target or target sequence refer to nucleic acid sequences to be amplified or detected. These include the original nucleic acid sequence to be amplified, its complementary second strand and either strand of a copy of the original sequence which is produced by replication or amplification. The target sequence may also be referred to as a template for extension of hybridized primers.

A detector oligonucleotide is an oligonucleotide which comprises a single-stranded 5' or 3' "tail" which hybridizes to the target sequence (the target binding sequence) and an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching.

Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing of the adjacent secondary structure or the entire target binding sequence may form a single-stranded 5' or 3' tail in the detector oligonucleotide. If a portion of the target binding sequence of the detector oligonucleotide is involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (i.e., a "hairpin") and the target binding sequence of the detector oligonucleotide is present as a single-stranded 3' tail, the target binding sequence may also extend 5' through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

The detector oligonucleotide further comprises a donor fluorophore and an acceptor dye linked at positions in the detector oligonucleotide such that the intramolecular base-pairing of the secondary structure brings the dyes into close spatial proximity and results in fluorescence quenching. Preferably neither dye is at the 3' terminus of the detector oligonucleotide when it is used as a primer, as a 3' terminal label may interfere with hybridization and/or extension of the oligonucleotide. However, a selected donor fluorophore or acceptor dye may be linked at any position which does not inhibit hybridization and/or extension, which results in quenching in the folded secondary structure and which provides a change in a fluorescence parameter upon unfolding or linearization. The donor and acceptor dyes are also linked such that unfolding of the secondary structure increases the distance between them and reduces fluorescence quenching, resulting in a detectable change in a fluorescence parameter.

The donor and an acceptor dye are linked to the detector oligonucleotide such that donor fluorescence is totally or partially quenched when the detector oligonucleotide forms the intramolecularly base-paired secondary structure. The two dyes must be in sufficiently close proximity when the secondary structure is folded so that quenching will occur. However, the distance between them in the linear nucleotide sequence of the detector oligonucleotide must provide for a change in proximity sufficient to produce a detectable change in a fluorescence parameter of either the donor or the acceptor when the secondary structure is unfolded or linearized. Both dyes may be linked to sequences involved in formation of the secondary structure at positions such that unfolding increases the distance between them. Alternatively, one dye may be linked in the secondary structure sequence and the other may be linked to the single-stranded target binding sequence, such that unfolding of the secondary structure increases the distance between them. Preferably, both dyes are linked to the detector oligonucleotide so that they are both incorporated into the secondary structure and are on opposite arms of an intramolecularly base-paired sequence (i.e., one dye in or near each of the two complementary sequences which are involved in intramolecular base-pairing).

If an RERS is present, the proximity of the dyes must also allow the restriction endonuclease access to the RERS in the linearized or unfolded structure for binding and cleavage/nicking when the target is present. In general, at least about eight nucleotides between the two dyes are necessary to provide sufficiently efficient cleavage or nicking by the restriction endonuclease. Preferably, there are at least about 11 nucleotides between the dyes when an RERS is present in the detector oligonucleotide. In general, the overall length of the sequence involved in intramolecular base-pairing in the secondary structure is not critical. The appropriate length is determined by the number of nucleotides required for folding and stable base-pairing in the selected secondary structure. For convenience it is typically between about 8 and 75 nucleotides in length. Longer sequences which form the secondary structure allow the donor and acceptor dyes to be linked such that they will be separated by greater distances in the linearized form than dyes linked to shorter secondary structure-forming sequences. For example, the longer the stem and/or the loop of a hairpin, the farther apart the dyes linked thereto will be when it is linearized. Sequences which form hairpins are simple to synthesize and are therefore preferred for use in the invention. Typically, at least about seven nucleotides are needed to form a stable hairpin. The maximum size is limited only by practical concerns such as the ease and efficiency of oligonucleotide synthesis and recovery. Hairpins comprising about 10–30 nucleotides are preferred for use in the invention because they provide good assay sensitivity but are small enough to be easily synthesized. Hairpin secondary structures are used as illustrative examples herein. However, any sequence which folds spontaneously into an ordered, intramolecularly base-paired secondary structure under the primer extension or hybridization conditions of the reaction is suitable for use in the detector oligonucleotides of the invention. These further include, but are not limited to, sequences which form triple helices or pseudoknots.

The sequence of the secondary structure in the detector oligonucleotide is preferably selected such that the intramolecularly base-paired secondary structure is less stable than the intermolecularly base-paired duplex which forms in the presence of target. The transition midpoint ($T_m$) is a useful means for estimating these relative stabilities, but other factors may also be considered. In general, the $T_m$ of the secondary structure when intramolecularly base-paired is preferably equal to or less than the $T_m$ of the intermolecularly base-paired duplex which forms in the presence of target. More preferably, the $T_m$ of the secondary structure is about 5–45° C. less than the $T_m$ of the intermolecularly base-paired duplex, most preferably about 10–25° C. less. This favors maintenance of the intermolecularly base-paired duplex over self-complementation and optimizes the total change in fluorescence by reducing "snap-back" of the detector oligonucleotide into the intramolecularly base-paired secondary structure, providing greater assay sensitivity when it is required. The sequence of the secondary structure is also selected such that it is relatively stable at the temperature of the reaction which serves to unfold or linearize it. However, it must not be so stable that hybridization to the target is unacceptably slow or so stable that the polymerase is unable to destabilize the secondary structure for synthesis of the complementary strand. Preferably, the $T_m$ of the secondary structure is equal to or greater than the temperature at which the unfolding or linearization reactions will occur, but it may be lower. If the $T_m$ of the secondary structure is less than the reaction temperature, more than half of the detector oligonucleotide molecules will be unfolded independent of the presence of the target. This reduces assay sensitivity but may be acceptable when relatively high quantities of target are present. Typically, the $T_m$ of the secondary structure is selected to be equal to or up to about 30° C. higher than the temperature of the unfolding or linearization reaction. Most preferably, the $T_m$ of the secondary structure is about 10–20° C. higher than the unfolding or linearization reaction temperature. To favor hybridization to target, the sequence of the single-stranded target binding tail region is also preferably selected such that the $T_m$ of the target binding sequence/target duplex is equal to or higher than the reaction temperature. Although the sequence of the target binding region is dictated by the sequence of the target, adjustments in the $T_m$ of the target binding sequence of the detector oligonucleotide may be made, for example, by adjusting its length.

Figure 1:
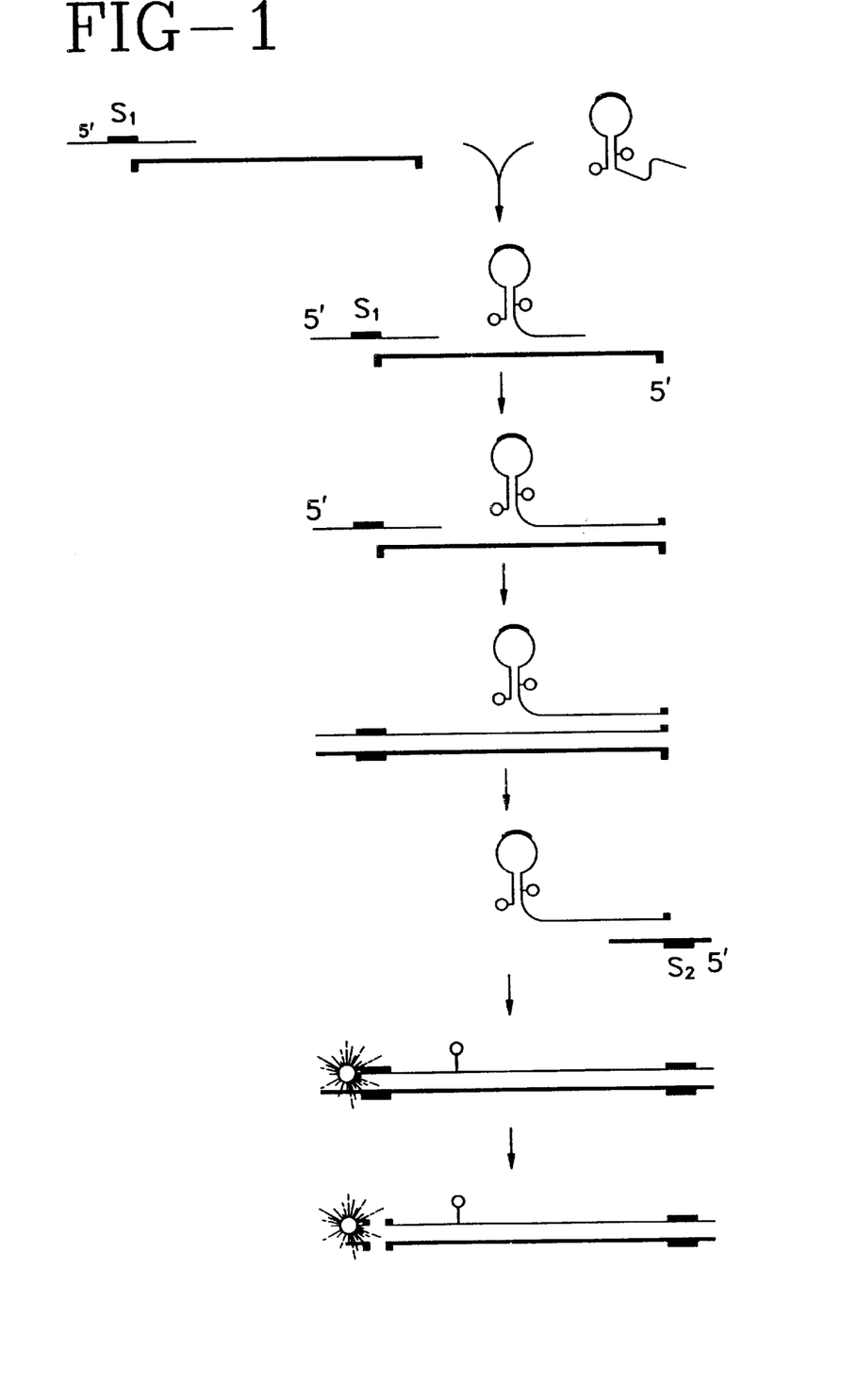
FIG. 1 illustrates the reaction scheme wherein the detector oligonucleotide is employed as a signal primer according to the invention.

Optionally, the donor and acceptor dyes may flank a restriction endonuclease recognition site (RERS) in the secondary structure as shown in the detector oligonucleotide depicted in FIG. 1 (raised box). That is, an RERS may be present in the secondary structure-forming sequence of the detector oligonucleotide at a position between the donor and acceptor dye. Inclusion of an RERS provides the advantage of permanent conversion of the detector oligonucleotide into a structural form which exhibits altered fluorescence, i.e., cleavage or nicking prevents reassociation of the detector oligonucleotide into the quenched structure. In this embodiment, folding of the secondary structure brings the dyes into close spatial proximity while the RERS remains partially or entirely single-stranded in an unbase-paired portion of the secondary structure between the two dyes. In the detector oligonucleotide, the RERS sequence corresponds to one strand of the double-stranded RERS. Either the donor or acceptor dye is linked to the detector oligonucleotide 3' to the RERS. The donor fluorophore (if the acceptor is 3' to the RERS) or the acceptor (if the donor is 3' to the RERS) is linked to the detector oligonucleotide at a position 5' to the RERS. That is, the donor and acceptor dyes flank the RERS. The dyes are preferably linked on either side of the RERS at positions sufficiently far apart to allow the restriction endonuclease access to the RERS for cleavage or nicking. At least about eight nucleotides between the dyes are typically necessary for sufficient cleavage or nicking of the RERS by the restriction endonuclease.

In a first embodiment, the detector oligonucleotides of the invention may be used as signal primers in an amplification reaction to generate double-stranded secondary amplification products with an accompanying change in a fluorescence parameter. When used as a signal primer in nucleic acid amplification reactions the single-stranded tail of the detector oligonucleotide is at the 3' end to allow for primer extension. The secondary structure is therefore 5' to the target binding sequence when the detector oligonucleotide is used as a signal primer. The term "5' to the target binding sequence" indicates that all or part of the target binding sequence is present as a single-stranded 3' tail. That is, the secondary structure may comprise a portion of the target binding sequence or the entire target binding sequence may be present in the single-stranded 3' tail. The detector oligonucleotide signal primer reaction is illustrated in FIG. 1 and may be summarized as follows. A detector oligonucleotide signal primer hybridizes to one strand of the target sequence downstream of an amplification primer. Both the amplification primer and the detector oligonucleotide are extended by DNA polymerase using the target sequence as a template. The detector oligonucleotide extension product is displaced from the template by extension of the upstream amplification primer and in turn serves as a template for hybridization and extension of a second amplification primer, rendering the detector oligonucleotide extension product double-stranded. A second detector oligonucleotide which hybridizes to the second, complementary strand of a double-stranded target sequence may optionally be included in the reaction (not shown in FIG. 1). The second detector oligonucleotide hybridizes to the second strand of the target sequence downstream of the second amplification primer and is extended and displaced by extension of the second amplification primer. The second detector oligonucleotide extension product is rendered double-stranded by hybridization and extension of the first amplification primer. Multiple detector oligonucleotides per strand of target may be employed if desired, each hybridizing to the target sequence downstream of the other on the same strand, and all detector oligonucleotides being hybridized downstream of the amplification primer. In this manner, each detector oligonucleotide is displaced by extension of the upstream detector oligonucleotide and the most 5' detector oligonucleotide is displaced by the amplification primer. Use of multiple detector oligonucleotides has the advantage of increasing or amplifying the signal generated per target, with an increase in sensitivity of the assay.

When used as a signal primer in SDA reactions, the detector oligonucleotide RERS, if present, may be a sequence which is recognized by the same restriction enzyme as provides the nicking function central to SDA. That is, two different recognition sequences for the same restriction endonuclease may be employed—one in the detector oligonucleotide signal primer and one in the amplification primer. In this embodiment, the sequence of the detector oligonucleotide RERS may be selected such that double-stranded cleavage is not prevented when the modified nucleotides of SDA are incorporated. In contrast, the sequence of the amplification primer RERS is selected such that nicking by the restriction endonuclease is induced by incorporation of modified nucleotides. For example, the CTCGAG and CCCGAG recognition sites for BsoBI remain cleavable when hemimodified, whereas the CTCGGG recognition site for the same enzyme is nicked when hemimodified. Alternatively, a recognition site for a restriction endonuclease different from that which provides the nicking function in the SDA reaction may be present in the detector oligonucleotide signal primer. Again, however, the RERS in the detector oligonucleotide signal primer is preferably selected such that double-stranded cleavage is not compromised by incorporation of modified nucleotides. In still another alternative embodiment, the RERS in the detector oligonucleotide is selected so as to be nicked once by the restriction endonuclease, regenerating an RERS which is not renickable upon repair by the polymerase and incorporation of the modified nucleotide. Such "singly-nickable" sites may be recognized by either the same restriction endonuclease which provides the nicking function in the SDA reaction or by a different restriction endonuclease. Singly nickable sites are generally canonical and contain a nucleotide at the nicking site which is the same as the modified deoxynucleoside triphosphate in the SDA reaction. For example, the CCCGGG recognition site for BsoBI is nicked between the first and second C's. When incorporated in a detector oligonucleotide signal primer in an SDA reaction employing dCTPαS, repair of the nick and displacement of the strand downstream of the nick incorporates the modified C nucleotide at the nicking site. Modification of the nicking site inhibits renicking, but the initial nick separates the donor and acceptor dyes by allowing strand displacement of the downstream fragment carrying one of the dyes. Singly nickable sites are desirable in the invention because they prevent amplification of the detector oligonucleotide signal primer independently of amplification of the target sequence.

When added to the amplification reaction, the detector oligonucleotide signal primers of the invention are converted to double-stranded form by hybridization and extension of an amplification primer as described above. Strand displacement by the polymerase also unfolds or linearizes the secondary structure and converts it to double-stranded form by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, linearization of the secondary structure and separation of the dye pair reduces fluorescence quenching, with a change in a fluorescence parameter such as intensity serving as an indication of target amplification.

For adaptation of the inventive methods to 3SR, TMA or NASBA, a 5'→3' exonuclease deficient reverse transcriptase with strand displacing activity is employed, with hybridization of the detector oligonucleotide to the RNA target downstream of an amplification primer which contains an RNA polymerase promoter. In a reaction scheme similar to that previously described, the hybridized detector oligonucleotide containing the secondary structure is 1) extended, and 2) displaced by extension of the upstream amplification primer. The displaced extension product is then made double-stranded by hybridization and extension of the second amplification primer. This unfolds or linearizes the secondary structure, increasing the distance between the donor and acceptor dyes and reducing fluorescence quenching of the donor fluorophore. The detector oligonucleotide signal primer for 3SR or NASBA does not contain an RNA polymerase promoter sequence and therefore cannot function as an amplification primer, reducing nonspecific background signal. This is analogous to the signal primer in SDA, which does not contain a nickable RERS and therefore does not significantly contribute to exponential background amplification of non-specific targets.

For reduced background, it is preferred that detector oligonucleotides be used as signal primers in the methods of the invention, with the detector oligonucleotide extension product being separated from the target sequence by displacement due to extension of the upstream amplification primer. However, it will be apparent that the amplification primers known for use in the various nucleic acid amplification reactions may also be modified by linkage of a 5' intramolecularly base-paired secondary structure as described for detector oligonucleotide signal primers. In this embodiment, the amplification primer extension product, with the 5' secondary structure, may be separated from the target sequence by displacement due to extension of an upstream non-amplification primer (e.g., bumper primers as in SDA), by denaturation (e.g., heating as in PCR) or by enzymatic digestion of the target strand (e.g., RNase H as in 3SR). Amplification primers comprising the 5' secondary structure and donor/acceptor dye pair eliminate the need for the additional detector oligonucleotide in the reaction, but because background may be higher in this embodiment the sensitivity of the assay may be decreased. For PCR, the amplification primer is modified by addition of the secondary structure 5' to the target binding sequence. This primer is structurally identical to the PCR detector oligonucleotide signal primer described above. Functionally, however, it is different in that there is no downstream primer to be extended and displaced and the amplification primer itself provides the change in fluorescence. For 3SR, NASBA and TMA, the secondary structure with the linked dyes may be placed 5' to the promoter of an amplification primer so that the secondary structure is unfolded or linearized in the double-stranded DNA portion of the amplification cycle. If an RERS is present, it is 5' to the promoter so that cleavage does not remove the promoter from the amplification primer and generation of RNA transcripts continues to sustain target amplification. A second amplification primer which does not contain a promoter sequence (e.g., as in NASBA) may also or alternatively contain the secondary structure 5' to the target binding sequence.

As intramolecularly base-paired secondary structures are very stable, it was not known whether or not the polymerase would be capable of strand displacing to linearize them under in vitro primer extension conditions. In particular, the intramolecular base-pairing of the secondary structure may place the two bulky dyes in close proximity on opposite arms of an intramolecularly base-paired duplex, and the ability of the polymerase to strand displace through two bulky dyes under in vitro conditions without stalling or dissociating from the DNA was uncertain. The efficiency of this function was considered even more unpredictable in SDA, where the efficiency of the polymerase is reduced by the necessity of incorporating modified nucleotides.

In alternative embodiments, the detector oligonucleotide may be used in non-amplification based assay formats to detect target oligonucleotides. In a first embodiment, the 3' single-stranded target binding sequence of the detector oligonucleotide hybridizes to the 3' end of the target oligonucleotide such that the base-paired secondary structure forms a 5' overhang. The target sequence functions as a primer in a primer extension reaction to synthesize the complement of the base-paired secondary structure using a strand displacing polymerase which extends the target sequence using the 5' overhang (i.e., the sequence of the base-paired secondary structure) as a template. If the target binding sequence of the detector oligonucleotide hybridizes to only a portion of the target sequence, the target sequence also forms a 5' overhang and the detector oligonucleotide is similarly extended using the 5' overhang of the target as a template. If the target binding sequence of the detector oligonucleotide is complementary to the entire length of the target sequence only the target is extended. In either case, the secondary structure of the detector oligonucleotide is thus unfolded or linearized with an accompanying change in fluorescence parameter. Extension to unfold or linearize the secondary structure and produce a change in fluorescence can take place only in the presence of target. Similarly, if an RERS is present, it can only be cleaved or nicked in the presence of target. As this method does not require SDA or any other amplification reaction, modified nucleotides are not necessary, and any RERS may be employed in the detector oligonucleotide. However, if the RERS is to be nicked rather than cleaved, modified nucleotides may be employed as described above to produce a singly nickable site.

In a second non-amplification based embodiment of the invention, the detector oligonucleotide is hybridized to the target sequence such that a change in fluorescence occurs. The single-stranded target binding sequence may therefore be at either the 5' or 3' end of the detector oligonucleotide when it is used as a hybridization probe. That is, as primer extension is not necessary the secondary structure may be either 5' or 3' to the single-stranded tail, optionally comprising a portion of the target binding sequence. In this embodiment, the secondary structure preferably comprises a portion of the target binding sequence with the remaining target binding sequence present in the 3' or 5' single-stranded tail which is available for non-competitive hybridization to the target. Hybridization thereby disrupts the secondary structure and results in unfolding. However, as shown in the following Examples, changes in fluorescence may also be observed upon hybridization when the target binding sequence is entirely in the single-stranded tail and no base-pairing between target and secondary structure is possible. When target is present, the detector oligonucleotide initially hybridizes to it by means of the single-stranded tail. This brings any target-complementary sequences of the secondary structure which may be present into close proximity with their complementary sequences in the target. The target binding sequence in the secondary structure hybridizes to its complementary sequence in the target, thus disrupting the intramolecular base-pairing in the secondary structure and increasing the distance between the donor and acceptor dyes as the secondary structure unfolds. The resulting change in a fluorescence parameter may be detected as an indication of the presence of the target sequence. Binding of the single-stranded 5' or 3' tail of the detector oligonucleotide to the target sequence is believed to facilitate disruption of the secondary structure by holding the complementary sequences of the target and the secondary structure in close proximity, better favoring intermolecular base-pairing. Such cooperative binding may allow the target to more effectively compete against the corresponding sequence in the detector oligonucleotide for hybridization to the complementary sequence in the secondary structure. Without cooperative binding provided by the single-stranded target binding sequence in the 3' or 5' tail of the detector oligonucleotide, the secondary structure would tend to remain intact and little or no change in fluorescence is likely to be observed even in the presence of target.

Bagwell teaches introduction of mismatches within the secondary structure to destabilize intramolecular base-pairing and allow the target to compete effectively against secondary structure formation. Adjusting secondary structure stability by introducing mismatches is a tedius and time-consuming process, as multiple trial-and-error attempts are generally necessary before a suitable balance of mismatches is identified for detection of a particular target. The detector oligonucleotides of the invention eliminate the need for mismatches in the secondary structure by providing a single-stranded target binding tail sequence positioned adjacent to the secondary structure so that when the detector oligonucleotide is hybridized to the target the secondary structure more readily unfolds.

The present invention also eliminates the need to place the target binding region of the probe in a loop of the secondary structure as taught by Tyagi, et al. (WO 95/13399). Typically, the loop must be 20–60 nucleotides in length to accommodate the target binding sequence. Selection of the loop must therefore be balanced against the selection of the intramolecularly base-paired portions of the secondary structure so that the structure remains stably folded in the absence of target but unfolds when target is present. This selection process is complicated by the fact that the thermostability of secondary structures containing large loops can be difficult to predict. In the secondary structures of the detector oligonucleotides of the invention there is no need for large and potentially unpredictable single-stranded loops because the target binding region resides in an adjacent tail sequence and, optionally, partially in an intramolecularly base-paired portion of the secondary structure. Although the target binding sequence may also include a loop of the secondary structure, the loop may be made smaller and therefore more predictable because the target binding sequence is primarily located in the adjacent 3' or 5' tail.

The present invention is also distinguished from the compositions and methods of Bagwell and Tyagi, et al. in that the target is not required to initially hybridize to the sequences of the secondary structure itself Initial competitive hybridization to the secondary structure as taught by Bagwell and Tyagi, et al. reduces the affinity of the probe for the target and decreases assay sensitivity. In contrast, the initial non-competitive binding of the invention better favors intermolecular hybridization in any subsequent competitive hybridization reaction. The length of the single-stranded 3' or 5' tail may be adjusted without affecting the thermodynamic properties of the secondary structure, so target hybridization may be optimized without requiring redesign of the secondary structure. This greatly simplifies detector probe design as compared to the prior art.

In addition to detecting the presence or absence of target and detecting amplification of a target, the inventive detector oligonucleotides and methods may be used as primers or hybridization probes to distinguish between targets which differ by one or more nucleotides. To perform such analyses, the target binding sequence in the single-stranded tail of the detector oligonucleotide is selected such that stable hybridization to the target occurs only when hybridization is enhanced by base-pairing of the target with one or more nucleotides involved in intramolecular base-pairing in the secondary structure. The detector oligonucleotide is further designed such that hybridization to a target containing one or more nucleotide differences to be detected would result in one or more mismatched base pairs in either the tail sequence or in the sequence of the secondary structure. The reduced stability of the mismatch in conjunction with competition from secondary structure formation reduces hybridization to the target containing the nucleotide difference(s), thus reducing the magnitude of the change in fluorescence as compared to a perfectly matched target (i.e., a target without the nucleotide difference). Increasing numbers of mismatches produce correspondingly smaller changes in fluorescence. Fewer mismatches result in correspondingly larger changes in fluorescence. As the number of mismatches decreases, the magnitude of the fluorescence change approaches that observed for perfectly matched sequences, with the ability to discriminate single nucleotide differences. Similar methods may be used to detect frame shift mutations.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format can be used to provide semi-quantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

Many donor/acceptor dye pairs known in the art are useful in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), N-(4-aminobutyl)-N-ethylisoluminol (ABEI)/TAMRA, and others. The selection of a particular donor/acceptor fluorophore pair is not critical. For energy transfer quenching mechanisms it is only necessary that the emission wavelengths of the donor fluorophore overlap the excitation wavelengths of the acceptor fluorophore, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Certain donor/acceptor pairs are exemplified above and in the following Examples, however, others will be apparent to those skilled in the art and are also useful in the invention. Any dye pair which produces fluorescence quenching in the detector oligonucleotides of the invention are suitable for use in the methods of the invention, regardless of the mechanism by which quenching occurs. It has been observed that N, N-modified tetramethyl indodicarbocyanine (Cy5) and ROX are an especially useful dye pair for use in the methods and detector oligonucleotides of the invention, providing a c hange in fluorescence of about 20-fold in the presence of target.

Terminal and internal labeling methods are also known in the art and may be used to link the donor and acceptor dyes at their respective sites in the detector oligonucleotide. Examples of 5'-terminal labeling methods include a) periodate oxidation of a 5'-to-5'-coupled ribonucleotide followed by reaction with an amine-containing label, b) condensation of ethylenediamine with a 5'-phosphorylated polynucleotide followed by reaction with an amine-reactive label, and c) introduction of an aliphatic amine substituent using an aminohexyl phosphite reagent in solid-phase DNA synthesis followed by reaction with an amine-reactive label. Labels may also be linked to synthetic DNA oligonucleotides at specific locations using special aliphatic amine-containing nucleotide phosphoramidite reagents. Selection of an appropriate method for linking the selected labels to the detector oligonucleotide and performing the linking reactions are routine in the art.

Target DNA for the following experimental examples was prepared from stocks of Chlamydia trachomatis elementary bodies (EB's) stored at concentrations of $10^6$ EB's/$\mu$L in 50% glycerol. EB stock solutions were diluted 1:10 in water, boiled for 15 minutes and prepared as 10-fold serial dilutions in 10 ng/$\mu$L human placental DNA. These stock solutions contained 1 to 100 genome copies/$\mu$L of target. The donor fluorophore was conjugated to the 5' phosphate. Measurements were obtained with an SLM 8100 research grade fluorometer equipped with a circulating bath for maintaining sample compartment temperature, a xenon arc lamp and grating monochromators for controlling excitation and emission wavelengths. Experiments with fluorescein (FAM) as the donor used 488 nm for the excitation wavelength and 525 nm for emission. Experiments in which ROX was the donor used an excitation at 580 nm and emission at 604 nm.

EXAMPLE 1

SDA was performed generally as described in EP 0 684 315, with addition of the detector oligonucleotide labeled at the 5' end with FAM and at T15 with ROX. The final concentrations of components in each 100 $\mu$L reaction were 40 mM $K_2PO_4$ pH 7.5, 6 mM MgOAc, 0.2 mM each dTTP, dGTP, dATP, 1.4 mM dCTPαS, 20 $\mu$g/mL acetylated BSA, 3% DMSO, 8% (v/v) glycerol, 100 ng human placental DNA, 25 units Bst polymerase (exo⁻ klenow fragment, New England BioLabs), 150 units AvaI (an isoschizomer of BsoBI, New England BioLabs, Beverly, Mass.), and DNA from 0, 10, 100 or 1,000 Chlamydia trachomatis elementary bodies. Each sample further contained the following primers:

SEQ ID NO:1 (Detector oligonucleotide, 50 nM, 5'-FAM/T15-ROX)

FAM-
TAGCACCCGAGTGCT$_{ROX}$AGAGTCT-
TCAAATATCAGAGCTTTACCTAACAA

SEQ ID NO:2 (Amplification primer S1.1, 750 nNM)
  ACCGCATCGAATCGATGTCTCGGGTA-
    GAAAATCGCATGCAAGATA
SEQ ID NO:3 (Amplification primer S2.1, 188 nM)
  CGATTCCGCTCCAGACTTCTCGGGAGCT-
    GCCTCAGAATATACTCAG
SEQ ID NO:4 (Bumper primer B1, 75 nM)
  TAAACATGAAAACTCGTTCCG
SEQ ID NO:5 (Bumper primer B2, 75 nM)
  TTTTATGATGAGAACACTTAAACTCA The italicized sequences in SEQ ID NO:1 form the base-paired stem of a hairpin structure. AvaI sites are shown bolded. The sequences 3' to the AvaI sites are target binding sequences complementary to the target. Each reaction was assembled to contain all reagents except Bst and AvaI, and the samples were then heated for 2 min. at 95° C. They were transferred to a 53.5° C. water bath for 3–5 min. and the enzymes were added for a total sample volume of 100 µL. The samples were then transferred to 225 µL cuvettes and placed into a research grade SLM 8100 spectrofluorometer (Spectronic Instruments, Rochester, N.Y.). The temperature of the cuvettes was maintained at 53–54° C. by a circulating water bath, and the fluorescence emission of each cuvette at 520 nm ($\gamma_{excitation}$=488 nm) was recorded every 8 sec. Reactions were typically followed for 60–90 min.

Figure 2:
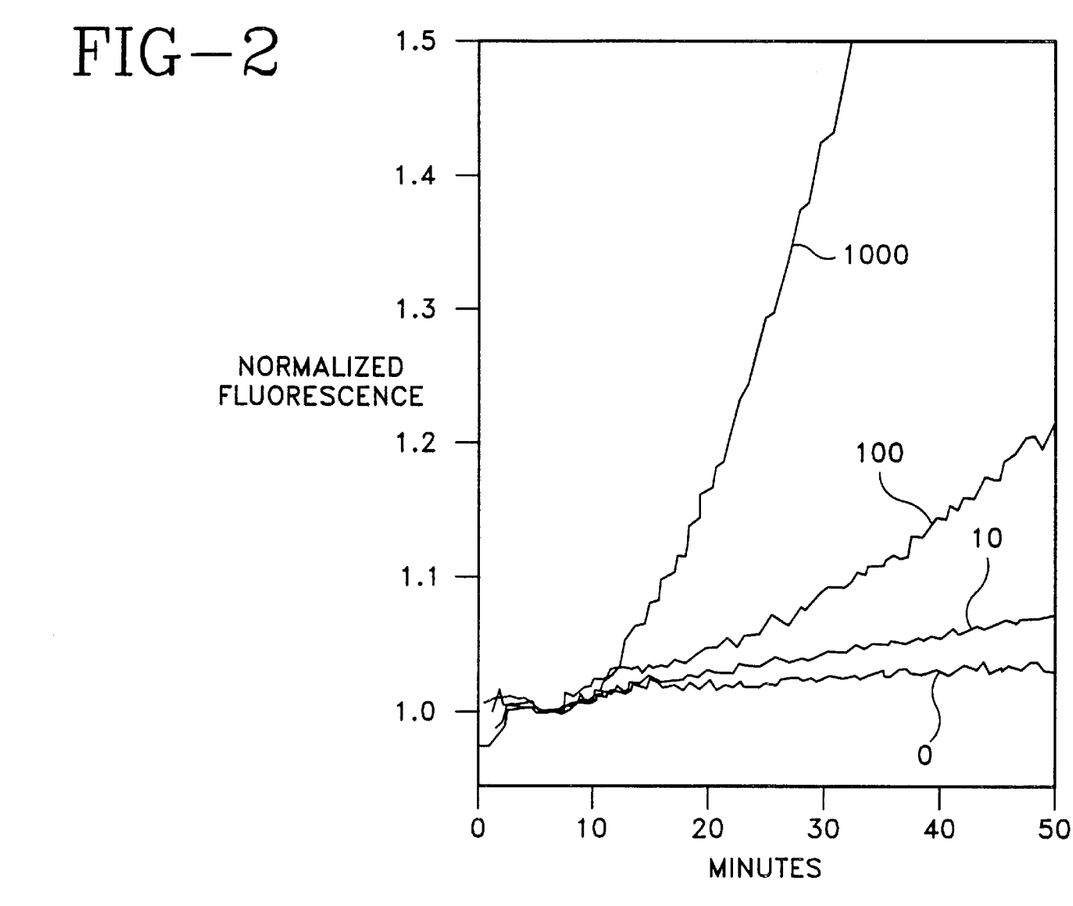
FIG. 2 shows the change in fluorescence intensity occurring in real-time as a target is amplified using the detector oligonucleotides of the invention as signal primers.

FIG. 2 shows the results. Fluorescence remained low (quenched) in the control reaction containing no target (no amplification) but increased significantly in reactions containing 10, 100 and 1,000 targets, demonstrating specific detection of target amplification. The sensitivity of this assay, in which the hairpin is converted to a linear, double-stranded conformation and cleaved, is about 10 genome copies of the target. The increase in fluorescence was about 8-fold for 1,000 genome copies, which is a greater change than is typically observed for cleavage alone with comparable amounts of target (typically an increase of about 5-fold). It is also about a 3-fold greater fluorescence change than is typically observed for unfolding of a hairpin without subsequent cleavage or nicking. These results indicate that by introducing a secondary structure into the detector oligonucleotide, the dye pair can be brought into close proximity to optimize quenching while at the same time maximizing the linear distance between the dyes in the presence of target. When an RERS is used alone, minimizing the distance between the dyes provides optimum quenching (and therefore maximum sensitivity to the assay) but also reduces the efficiency of cleavage or nicking due to physical blocking of the RERS by the bulky dyes, so dye separation in the presence of target is compromised. The present invention provides a solution to this problem and allows the practitioner to optimize both quenching and subsequent dye separation to improve the sensitivity of the assay.

In addition, the rate of increase in fluorescence intensity of the donor (a measure of the rate of decrease in donor quenching) was more rapid in samples containing higher initial amounts of target. The rate of increase in donor fluorescence therefore provides not only detection of amplification in real-time, but also a semi-quantitative or relative measure of initial target levels. Further, by comparing the rate of increase in fluorescence in a sample containing an unknown amount of target to the increase in fluorescence in a series of reactions containing varying known amounts of target (producing a standard curve as is known in the art) a quantitative measure of target levels in the unknown sample may be obtained. Alternatively, detection of an increase in fluorescence intensity above a predetermined threshold value may be used as an indication that the target is present and amplified in a simple positive/negative assay format. Alternatively, coamplification of the target or targets and an internal control sequence using the methods and detector oligonucleotides of the invention may be used as means for target quantitation. Several such coamplification methods are known in the art.

EXAMPLE 2

Synthetic target oligonucleotides (SEQ ID NOs:6–9) were designed to hybridize to a detector oligonucleotide according to the invention (SEQ ID NO:1), as shown below:

SEQ ID NO:6(JN5)

TTGTTAGGTAAAGCTCTGATATTTGAAGACTCATCTGAGTAACCAGAC

SEQ ID NO:7(JN6)

TTGTTAGGTAAAGCTCTGATATTTGAAGACTCTACTGAGTAACCAGAC

SEQ ID NO:8(JN7)

TTGTTAGGTAAAGCTCTGATATTTGAAGACTCTAGCGAGTAACCAGAC

SEQ ID NO:9(JN8)

TTGTTAGGTAAAGCTCTGATATTTGAAGACTCTAGCACGTAACCAGAC

SEQ ID NO:1(JBP70)

$_{FAM}$-*TAGCA*CCCGAGTGCT$_{ROX}$AGAGTCTTCAAATATCAGAGCTTTACC TAACAA

The two arms which form the intramolecularly base-paired stem of the hairpin of SEQ ID NO:10 are shown in italics. The first arm is unbolded and the second arm is bolded. The synthetic target sequences have a common 5' end comprised of thirty-two nucleotides which hybridize to the 3' end of SEQ ID NO:0 (the single-stranded 3' tail). Additional nucleotides of the various target sequences may also base-pair with SEQ ID NO:10 but this requires disruption of the intramolecular base-pairing of the stem of the hairpin, resulting in competition between the first arm of the stem and the target for hybridization to the second arm of the stem. The nucleotides of the target sequences which may potentially base-pair with SEQ ID NO:10 are underlined. SEQ ID NO:6 base-pairs with the detector oligonucleotide up to the junction between the hairpin stem and the 3' tail of SEQ ID NO:10, but does not base-pair with any stem nucleotides. SEQ ID NO:7 has the potential to base-pair with the 3' tail and two stem nucleotides adjacent to the 3' tail (shown bolded). SEQ ID NO:8 and SEQ ID NO:9 potentially pair with the 3' tail and four or six stem nucleotides adjacent to the 3' tail, respectively.

SEQ ID NO:10 (100 nM) was combined with a 5-fold molar excess of either SEQ ID NO:6, SEQ ID NO:7, SEQ ID NO:8 or SEQ ID NO:9 in potassium phosphate buffer under conditions suitable for hybridization. A sample containing no target served as a control. The solutions were excited at 488 nm and fluorescence emission of fluorescein (the donor) was measured at 520 nm (55° C.) after a period of time sufficient for hybridization.

The results are shown in the following Table:

TABLE

| TARGET | NORMALIZED FLUORESCENCE INTENSITY (520 nm) |
|---|---|
| None | 1.0 |
| SEQ ID NO:6 | 1.74 |
| SEQ ID NO:7 | 2.56 |
| SEQ ID NO:8 | 4.15 |
| SEQ ID NO:9 | 5.17 |

All target sequences were successfully detected by hybridization to the detector oligonucleotide. Unexpectedly, hybridization of SEQ ID NO:6 produced an increase in fluorescence even though base-pairing with the stem of the hairpin is not possible, suggesting that base-pairing near the secondary structure may lead to some disruption of intramolecular base-pairing. Under the assay conditions used, all target sequences should be stably hybridized to the single-stranded 3' tail of SEQ ID NO:10, so differences in fluorescence intensity may be attributed to differences in the extent of secondary structure disruption. Hybridization of SEQ ID NO:7, SEQ ID NO:8 and SEQ ID NO:9 showed that donor fluorescence intensity increases as the number of potential base-pairs between the target and the stem of the hairpin increases, indicating increasing unfolding of the secondary structure and increasing distance between the donor and acceptor dyes when the target and the detector oligonucleotide hybridize. The changes in fluorescence intensity most likely result from either a shift in the number of folded molecules or from a change in the average number of base-pairs per folded structure. These two mechanisms could not be distinguished in this experiment, but it was clearly demonstrated that the presence of target was required for a change in fluorescence to occur.

What is claimed is:

1. A method for detecting the presence of a nucleic acid target sequence comprising:
   a) hybridizing to the target sequence a detector oligonucleotide comprising a single-stranded target binding sequence and an intramolecularly base-paired secondary structure 5' to the target binding sequence, wherein at least a portion of the target binding sequence forms a single-stranded tail which is available for hybridization to the target sequence, the detector oligonucleotide having linked thereto a first dye and a second dye such that fluorescence of the first or second dye is quenched;
   b) in a primer extension reaction, synthesizing a complementary strand using the base-paired secondary structure as a template, thereby linearizing or unfolding the base-paired secondary structure and producing a change in a fluorescence parameter, and;

c) detecting the change in the fluorescence parameter as an indication of the presence of the target sequence.

2. The method of claim 1 wherein the base-paired secondary structure is selected from the group consisting of hairpins, stem-loop structures, pseudoknots and triple helices.

3. The method of claim 1 wherein the complementary strand is synthesized in a target amplification reaction.

4. The method of claim 1 wherein the complementary strand is synthesized by extension of the target sequence using the detector oligonucleotide as a template.

5. The method of claim 1 wherein the base-paired secondary structure comprises a totally or partially single-stranded restriction endonuclease recognition site.

6. The method of claim 1 wherein a change in fluorescence intensity is detected as an indication of the presence of the target sequence.

7. The method of claim 1 wherein the change in the fluorescence parameter is detected in real-time.

8. The method of claim 1 wherein the intramolecularly base-paired secondary structure comprises a portion of the target binding sequence.

9. A method for detecting amplification of a target sequence comprising, in an amplification reaction:
 a) hybridizing to the target sequence a detector oligonucleotide comprising a single-stranded target binding sequence and an intramolecularly base-paired secondary structure 5' to the target binding sequence, wherein at least a portion of the target binding sequence forms a single-stranded tail which is available for hybridization to the target sequence, the detector oligonucleotide having linked thereto a first dye and a second dye such that fluorescence of the first or second dye is quenched;
 b) extending the hybridized detector oligonucleotide on the target sequence with a polymerase to produce a detector oligonucleotide extension product and separating the detector oligonucleotide extension product from the target sequence;
 c) hybridizing a primer to the detector oligonucleotide extension product and extending the primer with the polymerase, thereby linearizing or unfolding the secondary structure and producing a change in a fluorescence parameter, and;
 d) detecting the change in the fluorescence parameter as an indication of amplification of the target sequence.

10. The method of claim 9 wherein the target sequence is amplified by Strand Displacement Amplification, Polymerase Chain Reaction, 3SR, TMA or NASBA.

11. The method of claim 9 wherein the secondary structure further comprises a partially or entirely single-stranded restriction endonuclease recognition site.

12. The method of claim 9 wherein a change in fluorescence intensity is detected.

13. The method of claim 12 wherein the change in fluorescence intensity is detected in real-time.

14. The method of claim 9 wherein the intramolecularly base-paired secondary structure comprises a portion of the target binding sequence.

15. A method for detecting a target sequence comprising:
 a) providing a detector oligonucleotide comprising a single-stranded target binding sequence and an intramolecularly base-paired secondary structure adjacent to the target binding sequence, wherein at least a portion of the target binding sequence forms a single-stranded 5' or 3' tail which is available for hybridization to the target sequence, the detector oligonucleotide having linked thereto a first dye and a second dye such that fluorescence of the first or second dye is quenched;
 b) hybridizing the detector oligonucleotide to the target sequence, thereby producing a change in a fluorescence parameter, and;
 c) detecting the change in the fluorescence parameter as an indication of the presence of the target sequence.

16. The method of claim 15 wherein the secondary structure comprises a portion of the target binding sequence.

17. The method of claim 15 wherein the intramolecularly base-paired secondary structure is 5' to the target binding sequence.

18. The method of claim 15 wherein the intramolecularly base-paired secondary structure is 3' to the target binding sequence.

19. The method of claim 15 wherein the change in the fluorescence parameter is a change in fluorescence intensity.

20. The method of claim 15 wherein the secondary structure is a hairpin.

21. The method of claim 9 wherein the secondary structure is a hairpin.

22. The method of claim 16 wherein the detector oligonucleotide hybridizes to the target sequence with at least one mismatch, thereby reducing the change in the fluorescence parameter as compared to hybridization of the detector oligonucleotide without the mismatch.

23. A method for detecting a nucleic acid target sequence comprising:
 a) hybridizing to the target sequence a detector oligonucleotide comprising a single-stranded target binding sequence and an intramolecularly base-paired secondary structure 5' to the target binding sequence, wherein at least a portion of the target binding sequence forms a single-stranded tail which is available for hybridization to the target sequence and the intramolecularly base-paired secondary structure comprises a partially or entirely single-stranded restriction endonuclease recognition site, the detector oligonucleotide having linked thereto a first dye and a second dye such that fluorescence of the first or second dye is quenched;
 b) in a primer extension reaction, synthesizing a complementary strand using the base-paired secondary structure as a template, thereby linearizing or unfolding the base-paired secondary structure, rendering the restriction endonuclease recognition site partially or entirely double-stranded and producing a change in a fluorescence parameter;
 c) optionally, cleaving or nicking the partially or entirely double-stranded restriction endonuclease recognition site, and;
 d) detecting the change in the fluorescence parameter as an indication of the presence of the target sequence.

24. The method of claim 23 wherein the complementary strand is synthesized in a target amplification reaction.

* * * * *